United States Patent [19]
Mutke

[11] 4,367,728
[45] Jan. 11, 1983

[54] ISOLATION APPARATUS

[76] Inventor: Hans G. Mutke, Drygalskiallee 117, 8000 Munich, Fed. Rep. of Germany

[21] Appl. No.: 184,299

[22] Filed: Sep. 5, 1980

[30] Foreign Application Priority Data

Sep. 7, 1979 [DE] Fed. Rep. of Germany ....... 2936256

[51] Int. Cl.³ .............................................. A61M 16/02
[52] U.S. Cl. ................................ 128/1 R; 128/205.26; 128/132 R
[58] Field of Search .................. 128/205.26, 202.12, 128/1 B, 1 R, 132 D, 1.3, 298, 299

[56] References Cited

U.S. PATENT DOCUMENTS

| | | | |
|---|---|---|---|
| 3,272,199 | 9/1966 | Mathews | 128/1 R |
| 3,483,494 | 12/1969 | Cromie | 128/1.3 |
| 4,026,286 | 5/1977 | Trexler | 128/205.26 |
| 4,275,719 | 6/1981 | Mayer | 128/1 R |

Primary Examiner—Henry J. Recla
Attorney, Agent, or Firm—Ostrolenk, Faber, Gerb & Soffen

[57] ABSTRACT

The disclosure concerns an isolation apparatus useful for medical, biological, chemical, physical, or the like experiments and treatments. A flexible envelope in the form of an elongated sack is divided lengthwise into a plurality of sealed sections. The envelope is a transparent material and also includes a viewing window into the interior. At least one glove is formed in the envelope. Exit and entrance tubes for liquids and gases enable pressurizing of the sections and inlet and outlet of fluids from the sections. There is a sealable lock at one end of the envelope. Sealable openings along the length of the envelope allow an object within the envelope to have portions thereof, e.g. arms of a body, project out of the envelope.

15 Claims, 8 Drawing Figures

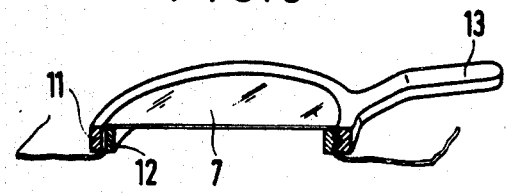
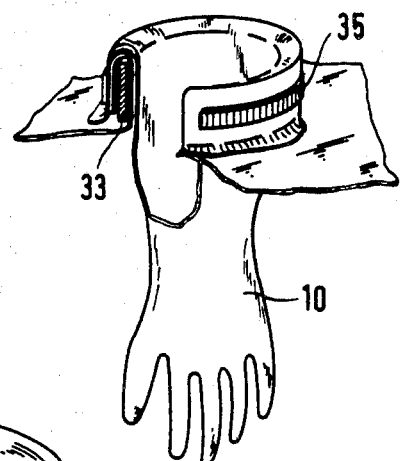
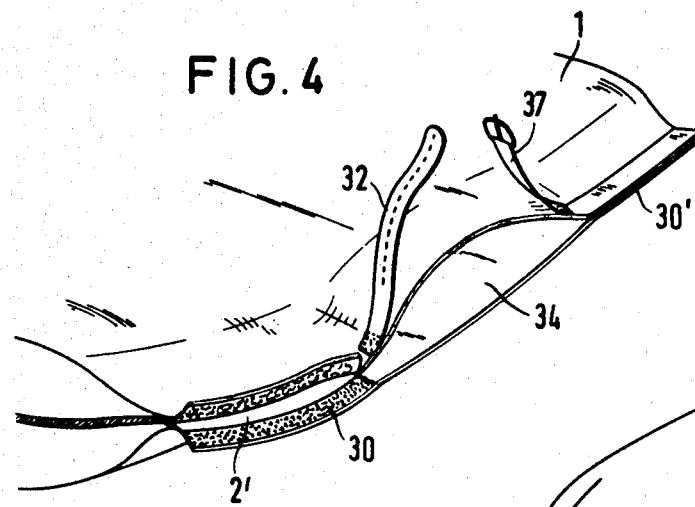
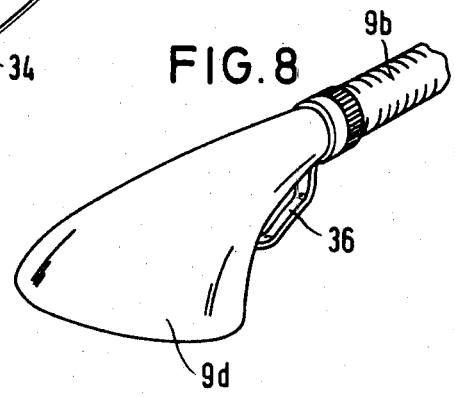
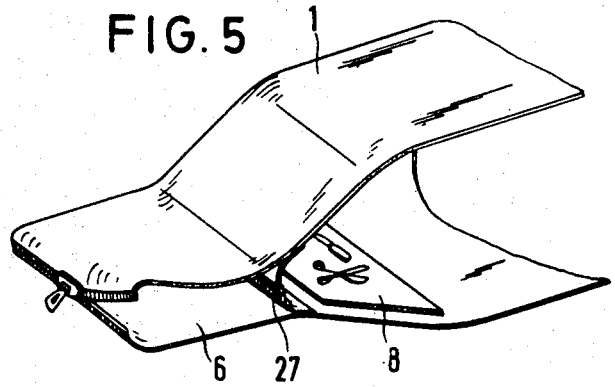

ISOLATION APPARATUS

The invention relates to an isolation apparatus for medical, biological, chemical, physical or other experiments and/or treatments in sealed surroundings wherein a substantially transparent envelope is provided which comprises transparent windows, gloves secured in sealed manner to the envelope and having long sleeves, and ventilation means.

A great number of medical isolation apparatus are known which start for example using a standardised hospital bed or a stretcher and comprise an envelope completely surrounding the patient and secured to a support frame. The envelope is provided with ventilating means for obtaining a predetermined pressure, preferably a reduced pressure within the envelope. The ventilating means communicate with the surrounding atmosphere via suitable filter means to prevent the emergence of pathogenic germs into the atmosphere. Furthermore, the envelope comprises a plurality of long-sleeved gloves disposed at suitable points permitting treatment of the patient within the envelope from the outside. These envelopes are usually made of transparent plastic sheets and may have additional transparent windows to improve the view of the patient. Further means secured to the envelope are for example lock means and means for keeping articles required in the treatment of the patient. The known medical isolation apparatus require a relatively large amount of space and are thus not suitable for many uses. One such use for example is in space travel. In future, using ferries known under the name "space shuttle" several persons will be in a laboratory on board such a space shuttle, serving as the crew of a space shuttle or carrying out research work on board the shuttle. It appears advisable to take precautions so that in the case of accidents or injury, for example explosions or other unpredictable incidents, treatment or at least provisional treatment of open wounds is possible. This requires not only corresponding training of the persons on board but the availability of suitable equipment for permitting such treatment to be carried out in weightlessness. Operations or experiments, such as birth in weightlessness, can be carried out only if special precautions are taken to ensure that the space craft is not contaminated with blood or other secretions. For this reason, isolation apparatuses are essential to enable such procedures to be carried out.

Similar problems also arise generally when carrying out technical, chemical, medical, biological or other experiments on board space craft in which in particular liquids or substances which are liberated can spread in an uncontrolled manner throughout the space craft due to the lack of gravity. Furthermore, it is not readily possible to conduct experiments involving the danger of fire on board space vehicles.

The object of the invention is to provide an isolation apparatus of the type mentioned at the beginning which has a low space requirement and low weight and which permits the execution of technical, chemical, medical, biological or other experiments and/or treatments under the conditions of weightlessness.

The isolation apparatus according to the invention has a low weight and low volume because it can be completely folded or rolled up. Due to the low weight and low volume a great number of such isolation apparatus may be carried on board a space vehicle and may be suitable both for carrying out technical, chemical, biological or other experiments and for medical treatment. For carrying out an experiment or treatment, one or more of the individual sections of the sack may be used and for carrying out large experiments or treatments, the closure means between adjacent sections of the sack may be opened so that a larger space or greater volume is available in the interior of the sack.

After performing the respective experiments and/treatments, possibly contaminated sections may be sealed and the content of these sections may be evaluated at a later time, for example after returning to earth, or may be destroyed without danger.

The isolation apparatus may have for example an inlet opening closable by sealing means or a lock for introducing or extracting articles serving to carry out the experiments and/or treatments. Furthermore, the instruments or materials required for a treatment or an experiment may be kept ready in the interior of the sack and for metallic instruments or the like pockets with magnetic attachments may preferably be provided. In this manner the instruments or articles are prevented from flying around in the weightless condition within the sack.

To minimize contamination of the interior of the sack, in particular when carrying out experiments and/or treatments in which large amounts of liquids occur, additional suction means are provided. These are within the interior of the sack and comprise nozzles for the extraction of the liquids liberated.

The sack may be inflated through the ventilating means with a controllable pressure thus permitting free working and experimenting within the interior thereof.

The isolation apparatus is necessary in any case for carrying out technical, physical, chemical or biological experiments and can readily be used in emergencies for medical treatment of persons. A suitable number of sections of the sack can be connected together by opening the sealing means disposed between the sections so that for example the entire trunk of a person can be accommodated by the sack and limbs of the person can conveniently project through passages provided in some of the sections. For this purpose, both the opening at the narrow side of the sack and the openings in the individual sections are provided with sealing means which permit the sack to bear air-tight on the trunk or the limbs of the person. In this manner it is also possible to carry out experiments and/or treatments on larger animals.

Even births are possible in the interior of the sack under the condition of weightlessness.

The invention will be explained in detail hereinafter with reference to examples of embodiments illustrated in the drawings, wherein:

FIG. 4 is a view of the upper narrow side of the embodiment of the isolation apparatus according to FIG. 2;

FIG. 5 is a partially sectioned view of the lower end of an embodiment of the isolation apparatus that can be used in the embodiment according to FIGS. 1 and 2;

FIG. 6 is an embodiment of a transparent window;

FIG. 7 is a partially sectioned view of an embodiment of the mounting of a glove on the envelope;

FIG. 8 is an view of the end of an embodiment of a suction means.

Figure 1:
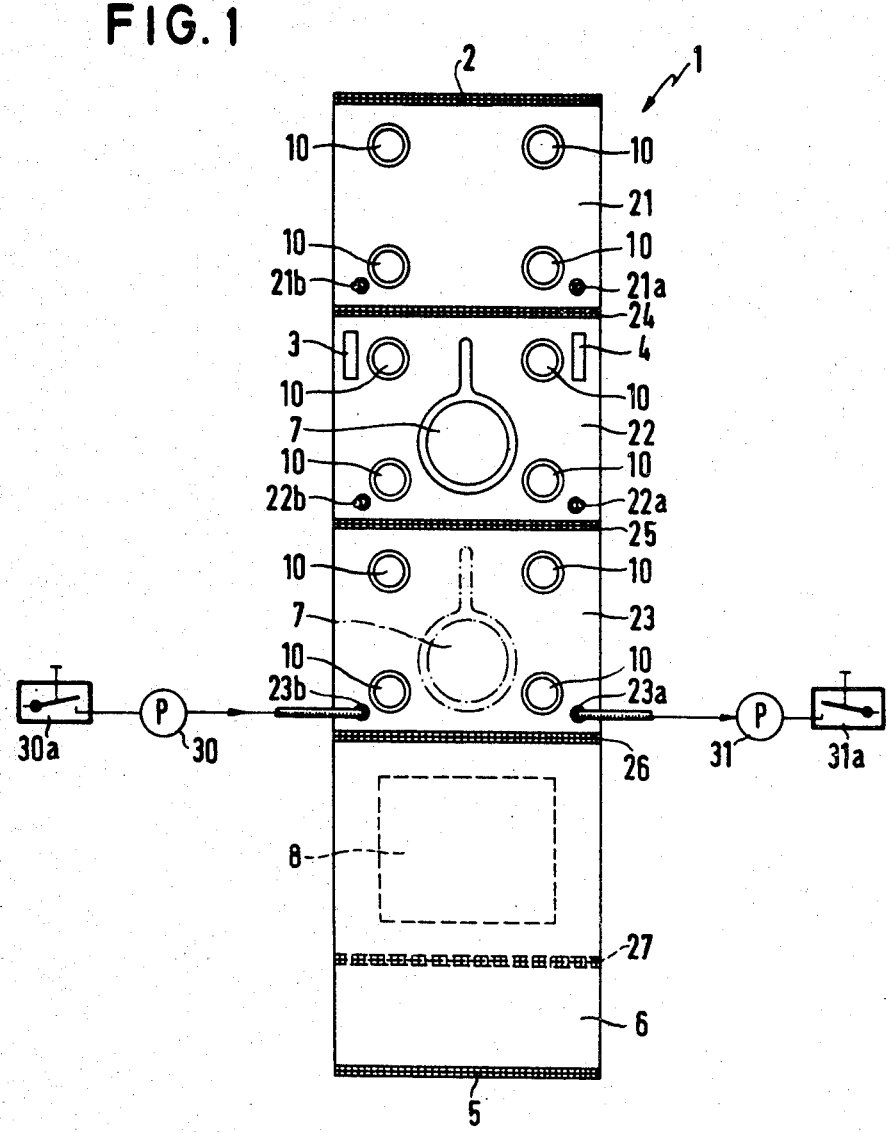
FIG. 1 is a plan view of an embodiment of the isolation apparatus.

FIG. 1 shows a first embodiment of an isolation apparatus which has the form of an elongated sack. At the upper narrow side in FIG. 1 there is an opening 2. A plurality of sealing means 24 to 27 divide the sack in the longitudinal direction. At the other narrow side 5 of the sack is an inlet opening closeable by sealing means in the form of a lock 6 for introducing and extracting articles necessary for carrying out experiments and/or treatment. In the section of the sack adjacent the lock 6 a pocket 8 is provided with magnetic adhesion for instruments necessary for carrying out experiments or treatment. In this manner such instruments can be prevented from flying about freely within the sack in the condition of weightlessness and they are always properly located within reach.

Each of the sections 21 to 23 of the sack is preferably provided with respective connections 21a to 23a and 21b to 23b for hoses leading to ventilation pump means, which are indicated for the section 23 diagrammatically at 30 and 31, together with associated actuating means such as switches 30a and 31a respectively. Furthermore, each section 21 to 23 comprises gloves 10 secured in air-tight manner to the sack 1 and shown more clearly in FIG. 2.

One or more of the sections are also provided with transparent windows 7 which will be explained hereinafter in detail with the aid of FIG. 6.

The sack 1 preferably consists of transparent plastic material so that the viewing windows can be formed simply by tensioning the plastic material with the aid of a frame.

In the section 22 of the sack the position of further openings 3, 4 is indicated diagrammatically. These openings permit, in the manner illustrated in FIG. 2, the passage of limbs, for example the legs of a person, when treatment has to be carried out in the trunk region of the person.

The embodiment of the sack illustrated in FIG. 1 may also be used for carrying out technical, physical, chemical, medical, biological or other experiments under the conditions of weightlessness. Even experiments which otherwise could not be carried out on board space craft because of the danger of fire may be performed within the sack 1 because the interior of said sack can for example be filled with a protective gas atmosphere such as nitrogen.

The materials and instruments necessary for carrying out the experiments may be stored before takeoff in one or more of the sections 21 to 23 and in the pockets 8 and the experiments may also be carried out in one or more of the individual sections of the sack 1. After performing the experiments individual sections of the sack may be sealed in air-tight manner and other experiments carried out in further sections of the sack. Waste products and test results of these experiments may be left in the individual sections until it is possible to evaluate them or destroy them without danger.

With the aid of the connection means 21a to 23a and 21b to 23b air or gas may be supplied to or extracted from the individual sections. By varying the amounts of air or gas supplied or extracted the pressure within the individual sections of the sack 1 may be varied so that an optimum inflation condition of the sack is always achieved, permitting unrestricted working in the interior of the sack.

Figure 2:
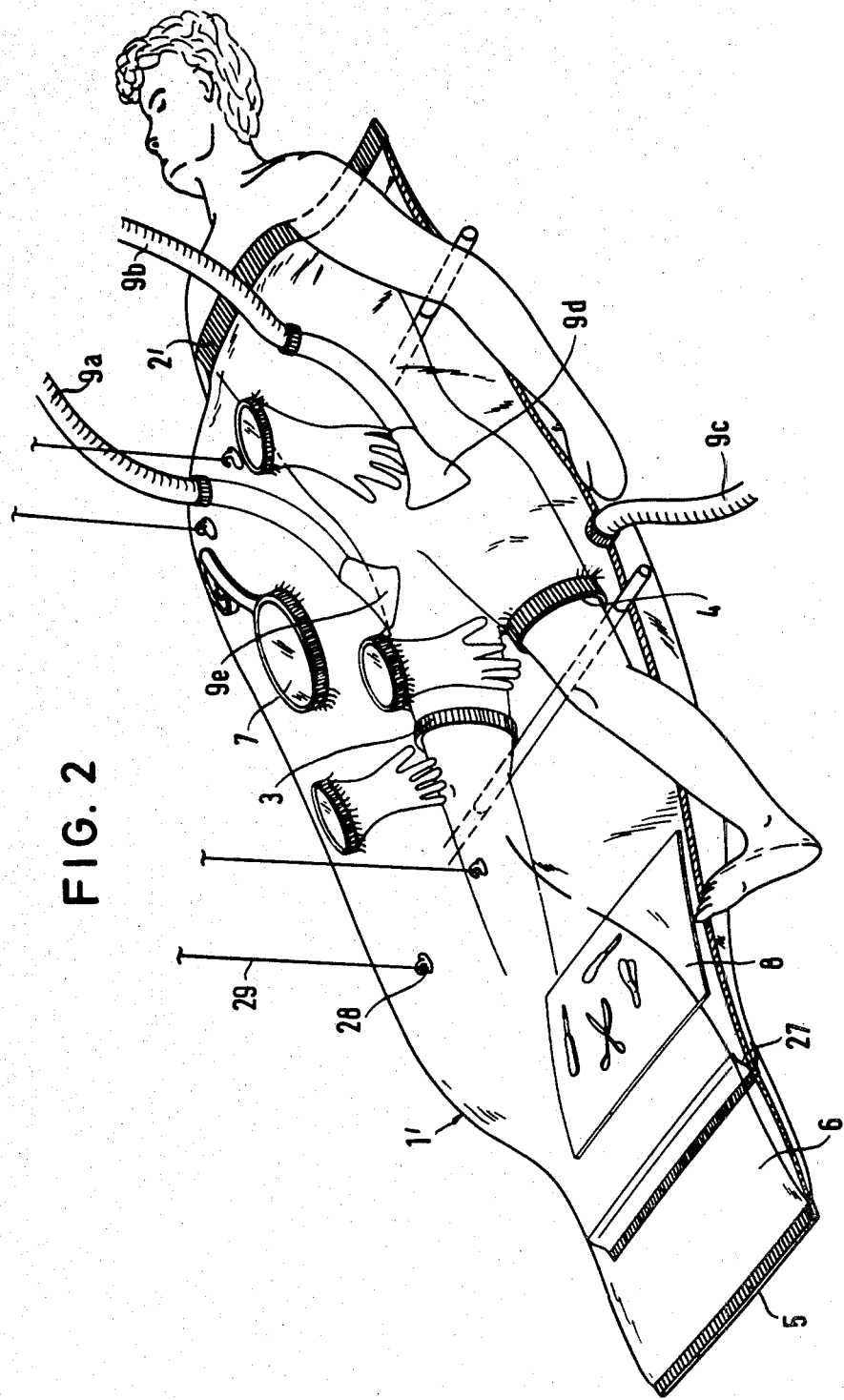
FIG. 2 illustrates use of the isolation apparatus according to FIG. 1.
Figure 3:
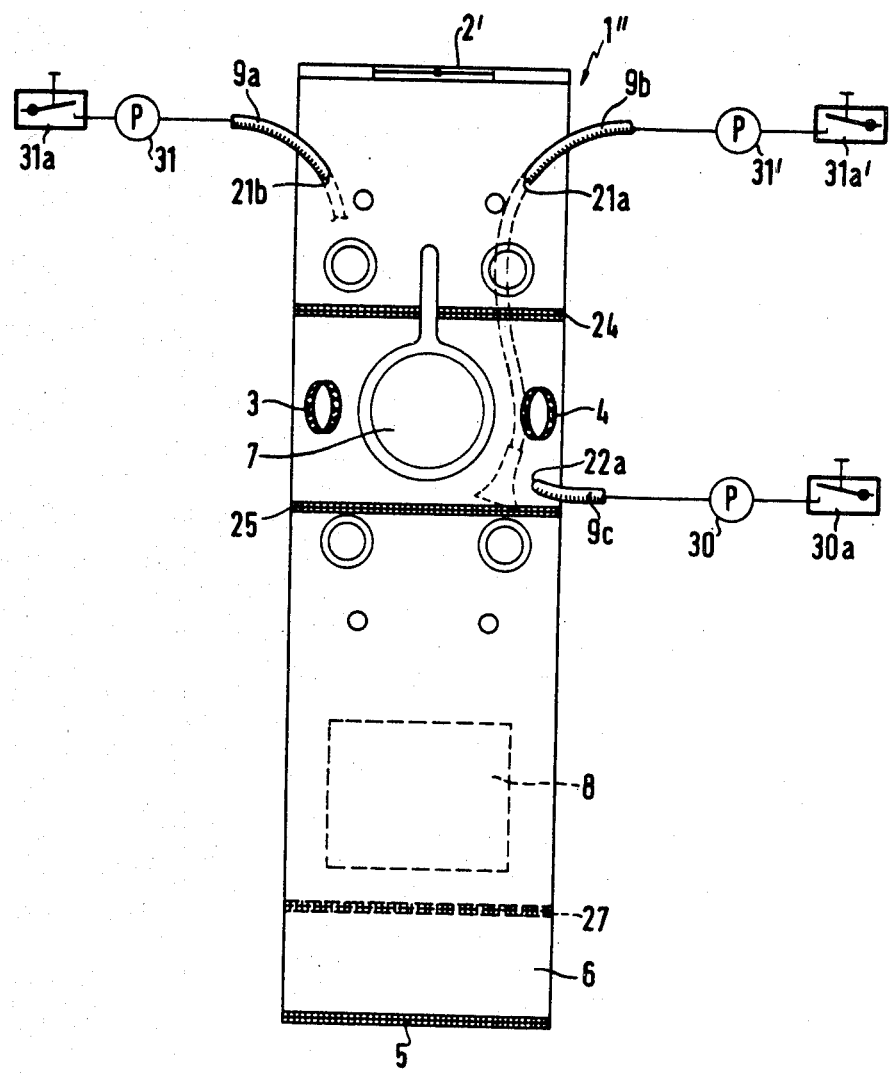
FIG. 3 is a plan view of a further embodiment of the isolation apparatus.

FIG. 2 shows a possible use of an embodiment of the isolation apparatus, said isolator being formed by a sack 1' which is fundamentally similar to the embodiments of FIGS. 1 and 3.

In this embodiment of the sack the sealing means are not illustrated, except for the sealing means 27 for the lock, but may be present in the same manner but open in the use according to FIG. 2. FIG. 2 indicates how a treatment is carried out on the trunk region of a patient in the sack.

The person is disposed in the sack so that the passage 2' at the upper narrow side encloses the trunk of the patient whilst the legs of the patient project outwards through the passages 3, 4. The connecting means for the ventilating means are connected on the one hand to a supply hose 9c and on the other to extraction hoses 9a and 9b which are connected in the interior of the sack via hose sections to suction nozzles 9d, 9e.

It is possible in this manner during the treatment to extract body liquids occuring very rapidly and effectively because the nozzles 9d, 9e may be brought to the necessary positions.

The instruments necessary for the treatment are disposed in the pockets 8 provided with magnetic adhesion so that when being used they are fixed and cannot fly about within the interior of the enclosure. The gloves disposed at the front of the sack 1' permit access to all regions within the sack and, depending on the number of gloves, several persons may participate in the treatment of the patients. Unrestricted observation of the interior of the sack is achieved with the transparent windows 7 which are provided with grips to enable the observation field to be varied and avoid reflection effects. The embodiment of the sack 1' shown in FIG. 1 is further provided with hooks, only one of which is designated with the reference numeral 28, which serve for securing holding cords 29 or the like preventing a collapsing of the sack 1' when using the latter under gravity. This makes it possible to use the isolation apparatus for other purposes as well, in which for example germ-free surroundings are required for treating a patient or carrying out experiments.

FIG. 3 shows a further embodiment of the isolation apparatus in the form of a sack 1" which is basically similar to the embodiment according to FIGS. 1 and 2 but compared with FIG. 1 has a smaller number of sealing means and thus of separate sections. Said sack 1" is provided with two suction means 31, 31a and 31', 31a' which lead to the suction nozzles 9d, 9e shown in FIG. 2. Furthermore, a supply means 30, 30a is provided for example for air.

Due to the reduced number of sections of the sack this embodiment is particularly suitable to the use shown in FIG. 2 because a great number of chambers is not necessary. The parts of the embodiment according to FIG. 3 corresponding to FIGS. 1 and 2 are designated by the same reference numerals. The embodiment according to FIG. 3 also comprises a modified passage opening 2' whose structure is more clearly shown in FIG. 4. This opening 2' comprises adhesion fasteners 30' which terminate in the region of an opening 34 whose magnitude can be varied by belts 32, 37 so that when used as in FIG. 2 a tight engagement of the upper end of the sack on the body of a patient is ensured. On the other hand, the openings 2, 2' according to FIGS. 1 and 3 may be used as well for arranging only part of a larger object on which experiments are to be conducted in the envelope, the opening being sealed in air-tight manner around the object.

FIG. 5 shows the foot portion of the embodiments of the sack according to FIGS. 1 to 3 partially in section so that the sealing means 27 and the pocket 8 provided with magnetic adhesion and instruments thereon are clearly apparent.

An embodiment of the transparent windows 7 is shown in detail in FIG. 6. This window 7 is formed by disposing a frame having an inner ring 12 and an outer ring 11 carrying a grip 13 at any point on the transparent sack, the inner ring 12 being pressed together with the region of the sack disposed thereabove into the outer ring 11 and said region of the sack tensioned so that unrestricted viewing is possible through this region of the sack.

FIG. 7 shows an embodiment of the glove 10 secured to the sack 1. A portion of the edge region of an opening in the sack 1 is placed around a rigid ring 33, about which the sleeve of the glove is folded and secured with the aid of a clamp band 35.

Finally, FIG. 8 shows an embodiment of the suction nozzle 9d which is connected to an extension of the hose 9b according to FIG. 2. This nozzle comprises a grip 36 permitting easy guiding of the suction nozzle to the particular working region.

I claim:

1. Isolation apparatus useful for medical, biological, chemical, physical or the like experiments and treatments in a sealed surrounding, comprising a flexible envelope in the form of an elongated sack; the sack being divided at spaced intervals along its length into at least two sections; a transparent window defined in the sack at at least one section of the sack for permitting viewing into the sack therethrough; a glove secured in sealed manner to the sack at at least said one section of the sack for enabling an operator to have access to an object connected to the sack at least said one section from the outside thereof; ventilation means in the sack for ventilating and inflating the sack with controllable pressure; a sealable passage opening into a side of the sack in said other section for through passage and holding therein of articles in the sack; at least one access opening into said one section for passing an object therethrough and into the sack wherein said object is adapted to be held in said access opening; said at least one access opening having means for airtight engagement of the periphery thereof about an object adapted to project and be held therein; selectively openable and closable sealing means at said spaced intervals along the length of and intermediate the length of the sack for dividing the sack into the at least two sections whereby the sections are separate from and selectively sealable from each other and are sealed from the environment.

2. The isolation apparatus of claim 1, wherein the sack comprises a substantially transparent envelope for permitting viewing of the interior of the sack.

3. The isolation apparatus of claim 1, wherein the sack has at least one narrow side and a second sealable passage opening at the one narrow side; said selectively openable and closable sealing means being disposed away from the one narrow side for defining said other section of the sack including the one narrow side therein.

4. The isolation apparatus of claim 1, further comprising a lock disposed away from the passage opening and provided in the sack for permitting introduction and removal of articles in said other section used for carrying out experiments and treatments; the lock comprising said other section of the sack with said passage opening providing entry from outside the sack, and selectively openable and closable sealing means in the sack between the lock and the next adjacent section of the sack.

5. The isolation apparatus of claim 4, wherein the sack has at least one narrow side and the sealable passage opening being at the one narrow side; the selectively openable and closable sealing means being disposed away from the one narrow side for defining said other section of the sack including the one narrow side therein;

the sack having a second narrow side opposite the one narrow side and the access opening being at the second narrow side.

6. The isolation apparatus of either of claim 1 or 4, further comprising wherein ventilation means for ventilating the sack include separate respective connection means for each of the sections of the sack for connecting each of the sections to the ventilation means; the connection means being sealable in an air tight manner when no ventilation is to occur through the ventilation means.

7. The isolation apparatus of claim 6, further comprising suction means communicating with at least said one of the sections of the sack for suctioning liquids or gases.

8. The isolation apparatus of claim 6, further comprising control means in said ventilation means for producing a respective predetermined pressure within the sections of the sack.

9. The isolation apparatus of claim 1, further comprising suction means communicating with at least said one of the sections of the sack for suctioning liquids or gases.

10. The isolation apparatus of claim 1, wherein said one section includes further access openings with said airtight engagement means so placed that one portion of an object adapted to be inserted inside the sack may project through the first mentioned access openings and other portions of that object may project through the further access openings, so that the projecting portions of that object may thereby project out of the sack.

11. The isolation apparatus of either of claims 1 or 2, wherein the entire sack is made integrally from transparent plastic material and wherein the transparent window comprises sections of the transparent plastic material which are tensioned, and tensioning means being provided for tensioning the plastic material at the window.

12. The isolation apparatus of claim 1, further comprising a pocket in the sack having magnetic adhesion means therein for enabling adherence thereto of metallic instruments by magnetic attraction for retaining the instruments in position.

13. The isolation apparatus of claim 1, wherein the ventilation means for ventilating the sack include separate respective connection means for each of the sections of the sack for connecting each of the sections to the ventilation means.

14. The isolation apparatus of claim 13, wherein the ventilation means comprises ports communicating to at least some of the sections of the sack for selectively communicating increased or decreased pressure to that section of the sack through the ports.

15. The isolation apparatus of claim 14, further comprising pressurizing means connected to one of the respective ports communicating to at least some of the sections of the sack and suction means connected to another one of the respective ports communicating to at least some of the sections of the sack for selectively pressurizing or suctioning materials out of the respective section of the sack to which the pressurizing means and suction means are connected.

* * * * *